(12) United States Patent
Pasqualucci (10) Patent No.: US 7,559,918 B2
(45) Date of Patent: *Jul. 14, 2009

(54) VALVE ASSEMBLY

(76) Inventor: Joseph Pasqualucci, 91 Scrub Oak Rd., North Haven, CT (US) 06743

( * ) Notice: Subject to any disclaimer, the term of this patent is extended or adjusted under 35 U.S.C. 154(b) by 0 days.

This patent is subject to a terminal disclaimer.

(21) Appl. No.: 11/085,303

(22) Filed: Mar. 21, 2005

(65) Prior Publication Data

US 2005/0165356 A1 Jul. 28, 2005

Related U.S. Application Data

(60) Division of application No. 10/611,712, filed on Jul. 1, 2003, now Pat. No. 6,923,783, which is a continuation of application No. 09/513,603, filed on Feb. 25, 2000, now Pat. No. 6,595,946.

(51) Int. Cl.
*A61M 5/178* (2006.01)
(52) U.S. Cl. ............. 604/164.02; 604/158; 604/167.01; 604/167.03; 604/264
(58) Field of Classification Search ............ 604/164.01, 604/164.06, 27, 158, 167.06, 246, 264; 277/355; 606/167, 185; 251/149.1, 149.2; 600/184
See application file for complete search history.

(56) References Cited

U.S. PATENT DOCUMENTS

| | | | |
|---|---|---|---|
| 3,421,509 A | 1/1969 | Fiore | |
| 3,565,078 A | 2/1971 | Vailliancourt et al. | |
| 3,853,127 A | 12/1974 | Spademan | |
| 3,907,310 A | 9/1975 | Dufour | |
| 3,994,287 A | 11/1976 | Turp et al. | |
| 4,000,739 A | 1/1977 | Stevens | |
| 4,112,932 A | 9/1978 | Chiulli | |
| 4,173,350 A | 11/1979 | Sieghartner | |
| 4,177,814 A | 12/1979 | Knepshield et al. | |
| 4,177,997 A | 12/1979 | Cartwright | |
| 4,202,554 A | 5/1980 | Snell | |
| 4,240,335 A | 12/1980 | Stucka et al. | |
| 4,240,411 A | 12/1980 | Hosono | |

(Continued)

FOREIGN PATENT DOCUMENTS

DE 3217118 8/1983

(Continued)

*Primary Examiner*—Patricia Bianco
*Assistant Examiner*—Camtu T. Nguyen (57) ABSTRACT

A valve assembly for the sealed reception of an elongated object is provided. The assembly includes a valve body defining at least one opening configured and dimensioned to permit entry of an elongated object and defining a central longitudinal axis, and an elongated seal member having a resilient sealing structure and defining an aperture in general alignment with the opening of the valve body whereby the aperture is configured and dimensioned such that upon insertion of the object into the aperture, the resilient sealing structure resiliently engages the outer surface of the object in a tight manner. The sealing structure includes a plurality of elongated bristle members attached to the seal member. The bristle members are positioned to engage the elongated object upon at least partial insertion of the elongated object into the valve body. Each bristle member is adapted to be displaced relative to the longitudinal axis to facilitate expansion of the aperture of the seal member upon entry of the elongated object therein.

13 Claims, 10 Drawing Sheets

U.S. PATENT DOCUMENTS

| | | | |
|---|---|---|---|
| 4,311,315 A | 1/1982 | Kronenberg | |
| 4,334,688 A | 6/1982 | Spargo et al. | |
| 4,338,689 A | 7/1982 | Zieg | |
| 4,386,756 A | 6/1983 | Muchow | |
| 4,387,879 A | 6/1983 | Tauschinski | |
| 4,430,081 A | 2/1984 | Timmermans | |
| 4,447,237 A | 5/1984 | Frisch et al. | |
| 4,464,178 A | 8/1984 | Dalton | |
| 4,468,224 A * | 8/1984 | Enzmann et al. | 604/247 |
| 4,553,760 A | 11/1985 | Reed et al. | |
| 4,588,195 A | 5/1986 | Antonini et al. | |
| 4,595,207 A | 6/1986 | Popp | |
| 4,601,710 A | 7/1986 | Moll | |
| 4,626,245 A | 12/1986 | Weinstein | |
| 4,641,842 A | 2/1987 | Kataoka | |
| 4,654,030 A | 3/1987 | Moll et al. | |
| 4,655,752 A | 4/1987 | Honkanen et al. | |
| 4,673,393 A | 6/1987 | Suzuki et al. | |
| 4,705,511 A | 11/1987 | Kocak | |
| 4,715,360 A | 12/1987 | Akui et al. | |
| 4,723,550 A | 2/1988 | Bales et al. | |
| 4,758,225 A | 7/1988 | Cox et al. | |
| 4,779,904 A | 10/1988 | Rich | |
| 4,842,591 A | 6/1989 | Luther | |
| 4,844,483 A | 7/1989 | Iijima et al. | |
| 4,844,484 A | 7/1989 | Antonini et al. | |
| 4,857,062 A | 8/1989 | Russell | |
| 4,869,717 A | 9/1989 | Adair | |
| 4,874,378 A | 10/1989 | Hillstead | |
| 4,889,349 A | 12/1989 | Muller | |
| 4,909,798 A | 3/1990 | Fleischhacker et al. | |
| 4,917,668 A | 4/1990 | Haindl | |
| 4,929,235 A * | 5/1990 | Merry et al. | 604/167.04 |
| 4,932,633 A | 6/1990 | Johnson et al. | |
| 4,943,280 A | 7/1990 | Lander | |
| 4,960,412 A | 10/1990 | Fink | |
| 4,966,588 A | 10/1990 | Rayman et al. | |
| 4,971,336 A | 11/1990 | Ferguson | |
| 4,989,919 A * | 2/1991 | Greer | 300/10 |
| 4,998,740 A | 3/1991 | Tellier | |
| 5,000,745 A | 3/1991 | Guest et al. | |
| 5,002,557 A | 3/1991 | Hasson | |
| 5,015,000 A | 5/1991 | Perini | |
| 5,029,875 A | 7/1991 | Spain | |
| 5,038,756 A | 8/1991 | Kepley | |
| 5,041,095 A | 8/1991 | Littrell | |
| 5,053,014 A | 10/1991 | Van Heugten | |
| 5,053,016 A | 10/1991 | Lander | |
| 5,073,169 A | 12/1991 | Raiken | |
| 5,104,383 A | 4/1992 | Schichman | |
| 5,127,626 A | 7/1992 | Hilal et al. | |
| 5,137,520 A | 8/1992 | Maxson et al. | |
| 5,167,636 A | 12/1992 | Clement | |
| 5,180,373 A | 1/1993 | Green et al. | |
| 5,197,955 A | 3/1993 | Stephens et al. | |
| 5,201,530 A * | 4/1993 | Kelch et al. | 277/355 |
| 5,201,714 A | 4/1993 | Gentelia et al. | |
| 5,209,736 A | 5/1993 | Stephens et al. | |
| 5,209,737 A | 5/1993 | Ritchart et al. | |
| 5,221,264 A | 6/1993 | Wilk et al. | |
| 5,226,891 A | 7/1993 | Bushatz et al. | |
| 5,242,412 A * | 9/1993 | Blake, III | 604/167.01 |
| 5,290,304 A | 3/1994 | Storace | |
| 5,299,813 A | 4/1994 | McKenna | |
| 5,300,036 A | 4/1994 | Mueller et al. | |
| 5,308,336 A | 5/1994 | Hart et al. | |
| 5,316,318 A | 5/1994 | Veau | |
| 5,320,611 A | 6/1994 | Bonutti et al. | |
| 5,342,315 A | 8/1994 | Rowe et al. | |
| 5,354,280 A | 10/1994 | Haber et al. | |
| 5,380,288 A | 1/1995 | Hart et al. | |
| 5,385,553 A | 1/1995 | Hart et al. | |
| 5,391,153 A | 2/1995 | Haber et al. | |
| 5,395,342 A | 3/1995 | Yoon | |
| 5,400,586 A | 3/1995 | Bagepalli et al. | |
| 5,407,433 A | 4/1995 | Loomas | |
| 5,411,483 A | 5/1995 | Loomas et al. | |
| 5,429,609 A | 7/1995 | Yoon | |
| 5,439,455 A | 8/1995 | Kieturakis et al. | |
| 5,443,452 A | 8/1995 | Hart et al. | |
| 5,474,305 A | 12/1995 | Flower | |
| 5,480,165 A | 1/1996 | Flower | |
| 5,485,553 A | 1/1996 | Kovalick et al. | |
| 5,496,280 A | 3/1996 | Vandenbroek et al. | |
| 5,542,582 A * | 8/1996 | Ligon et al. | 222/342 |
| 5,545,142 A | 8/1996 | Stephens et al. | |
| 5,554,124 A | 9/1996 | Alvarado | |
| 5,568,931 A | 10/1996 | Tseng et al. | |
| 5,584,850 A | 12/1996 | Hart et al. | |
| 5,603,702 A | 2/1997 | Smith et al. | |
| 5,628,732 A | 5/1997 | Antoon, Jr. et al. | |
| 5,634,908 A | 6/1997 | Loomas | |
| 5,643,227 A | 7/1997 | Stevens | |
| 5,643,301 A | 7/1997 | Mollenauer | |
| 5,709,664 A | 1/1998 | Vandenbroek et al. | |
| 5,743,884 A | 4/1998 | Hasson et al. | |
| 5,752,938 A | 5/1998 | Flatland et al. | |
| 5,782,812 A | 7/1998 | Hart et al. | |
| 5,782,817 A | 7/1998 | Franzel et al. | |
| 5,792,113 A | 8/1998 | Kramer et al. | |
| 5,827,228 A | 10/1998 | Rowe | |
| 5,857,999 A | 1/1999 | Quick et al. | |
| 5,868,714 A | 2/1999 | Danks | |
| 5,944,320 A | 8/1999 | Werner et al. | |
| 5,989,224 A | 11/1999 | Exline et al. | |
| 5,997,515 A | 12/1999 | De la Torre et al. | |
| 6,042,119 A | 3/2000 | Bagepalli et al. | |
| RE36,702 E | 5/2000 | Green et al. | |
| 6,210,064 B1 | 4/2001 | White et al. | |
| 6,228,061 B1 | 5/2001 | Flatland et al. | |
| 6,267,381 B1 * | 7/2001 | Wright | 277/355 |
| 6,276,661 B1 | 8/2001 | Laird | |
| 7,241,307 B2 * | 7/2007 | Lennox | 607/104 |

FOREIGN PATENT DOCUMENTS

| | | |
|---|---|---|
| EP | 0051718 | 5/1982 |
| EP | 0113520 | 7/1984 |
| EP | 0312219 | 4/1989 |
| EP | 0 316 096 B1 | 5/1989 |
| EP | 0696459 | 2/1996 |
| GB | 1482857 | 8/1977 |
| WO | WO 93/04717 | 3/1993 |
| WO | WO 98/53865 | 12/1998 |
| WO | WO 99/52577 | 10/1999 |

* cited by examiner

VALVE ASSEMBLY

CROSS REFERENCE TO RELATED APPLICATIONS

This application is a divisional U.S. patent application Ser. No. 10/611,712, filed on Jul. 1, 2003, now U.S. Pat. No. 6,923,783 which is a continuation of U.S. patent application Ser. No. 09/513,603, filed on Feb. 25, 2000, now U.S. Pat. No. 6,595,946. The priority of these prior applications is expressly claimed and the disclosures of which are hereby incorporated by reference in their entirety

BACKGROUND

1. Technical field

The present disclosure relates to valve assemblies of the type adapted to allow the introduction of a surgical instrument into a patient's body. In particular, the disclosure relates to a valve assembly to be used in combination with a cannula assembly where the cannula assembly is intended for insertion into a patient's body and an instrument is inserted into the patient's body through the cannula.

2. Background of Related Art

Laparoscopic procedures are performed in the interior of the abdomen through a small incision, e.g., through narrow endoscopic tubes or cannulas inserted through a small entrance incision in the skin. Minimally invasive procedures are performed elsewhere in the body, e.g., in the chest, and are often generally referred to as "endoscopic" procedures. Minimally invasive or endoscopic procedures generally require that any instrumentation inserted into the body be sealed, i.e. provisions must be made to ensure that gases do not enter or exit the body through the endoscopic incision as, for example, in surgical procedures in which the surgical region is insufflated. Moreover, endoscopic procedures often require the surgeon to act on organs, tissues, and vessels far removed from the incision, thereby requiring that any instruments used in such procedures be relatively long and narrow.

For such procedures, the introduction of a tube into certain anatomical cavities such as the abdominal cavity is usually accomplished by use of a system incorporating a trocar and cannula assembly. A cannula assembly is formed of a cannula attached to a cannula housing which generally includes valve assembly adapted to maintain a seal across the opening of the valve assembly both with and without an instrument inserted therethrough. Since the cannula is in direct communication with the internal portion of the valve assembly, insertion of the cannula into an opening in the patient's body so as to reach the inner abdominal cavity should be adapted to maintain a tight interface between the abdominal cavity and the outside atmosphere.

Since minimally invasive surgical procedures in the abdominal cavity of the body generally require insufflating gases to raise the cavity wall away from vital organs, the procedure is usually initiated by use of a Verres needle through which a gas is introduced into the body cavity. The gas provides a slight pressure which raises the wall surface of the peritoneum away from the vital organs thereby providing an adequate region in which to operate. Thereafter, a trocar assembly which includes a cannula and a trocar or obturator is inserted within the cannula to puncture the peritoneum, i.e. the inner lining of the abdominal cavity wall. The obturator is removed and laparoscopic or endoscopic surgical instruments may then be inserted through the cannula to perform surgery within the abdominal cavity. The cannula may also be utilized for introducing tubes into the body as for drainage purposes, for specimen removal, for diagnostic evaluations, or the like.

In view of the need to maintain the atmospheric integrity of the inner area of the cavity, a valve assembly for a cannula which permits introduction of an obturator and a wide range of surgical instruments and which maintains the atmospheric integrity of the inner area of the cavity is desirable. Generally, in the context of insufflatory, minimally invasive surgical procedures, cannula assemblies include structure(s) that satisfy two sealing requirements. The first requirement is to provide a tight seal when an instrument is not present in the cannula. The second requirement is to provide a tight seal when an instrument is being introduced into or already is present in the cannula. In this regard, there have been a number of attempts in the prior art to provide such sealing requirements.

A disadvantage of several known valve assemblies for cannulas, however, concerns the difficulty encountered in inserting and advancing the surgical instrument through the valve unit. In particular, since known elastomeric seal members are designed to form and maintain a tight seal about the instrument, the aperture or slit within the seal through which the instrument is passed is of relatively small or narrow dimension. Further, portions of the valve member defining the aperture are generally thick in cross-section to provide a sufficient closing force of the seal about the instrument. As a consequence of some of these design considerations, the level of force needed to insert and advance the instrument through the seal aperture is increased, thereby requiring awkward maneuvering on the surgeon's behalf to appropriately position the instrument for the desired surgery. Moreover, some known valve assemblies are generally ineffectual in accommodating instruments of differing diameter while maintaining acceptable insertion forces and facilitating the range of desired surgical manipulations, e.g., angular instrument movements and specimen removal.

Accordingly, a need exists for an improved valve unit or cannula assembly which is capable of forming and maintaining a seal about instruments of varying diameters inserted through the cannula and which incorporates structure to enhance and facilitate passage of the instrument through the valve unit.

SUMMARY

The present invention obviates the disadvantages of the prior art by providing a valve unit or assembly for a cannula assembly. Generally stated, the present disclosure is directed to a valve assembly for sealed reception of an elongated object. The assembly includes a valve body defining at least one opening configured and dimensioned to permit entry of an elongated object and defining a central longitudinal axis, and an elongated seal member having a resilient sealing structure and defining an aperture in general alignment with the opening of the valve body whereby the aperture is configured and dimensioned such that upon insertion of the object into the aperture, the resilient sealing structure resiliently engages the outer surface of the object in a tight manner. The sealing structure includes a plurality of elongated bristle members attached to the seal member. The bristle members are positioned to engage the elongated object upon at least partial insertion of the elongated object into the valve body. Each bristle member is adapted to be displaced relative to the longitudinal axis to facilitate expansion of the aperture of the seal member upon entry of the elongated object therein.

In a preferred embodiment, the valve assembly includes a valve body defining a longitudinal opening configured and dimensioned to permit entry of an elongated object, an elongated resilient seal member at least partially positioned within the valve body and defining an aperture to permit entry of the elongated object therein in a tight manner and a plurality of bristle members attached to the seal member and concentrically arranged about the central longitudinal axis of the valve body. The plurality of bristle members are positioned to engage the elongated object upon insertion of the elongated object within the valve body and are adapted to be displaced upon introduction of the elongated object to engage portions of the seal member defining the aperture to expand the aperture.

The bristle members of this embodiment are preferably linearly mounted on a substrate and extend generally perpendicularly with respect to the inner surface of the seal member. Upon entry of the elongated object, the bristle members simultaneously pivot downwardly to uniformly open or expand the aperture.

The valve assembly is intended to be used in combination with a cannula including a cannula housing and a cannula sleeve extending distally from the cannula housing and is preferably detachably connected to the cannula housing. The cannula housing may include a valve member disposed therein which is moveable between a substantially closed position in the absence of an instrument to an open position in the presence of an instrument.

BRIEF DESCRIPTION OF THE DRAWINGS

Various embodiments are described hereinbelow with reference to the drawings wherein.

DETAILED DESCRIPTION OF PREFERRED EMBODIMENTS

The present disclosure contemplates the introduction into a person's body of all types of surgical instruments including clip appliers, graspers, dissectors, retractors, staplers, laser fibers, photographic devices, endoscopes and laparoscopes, tubes, and the like. All such objects are referred to herein as "instruments".

Figure 1:
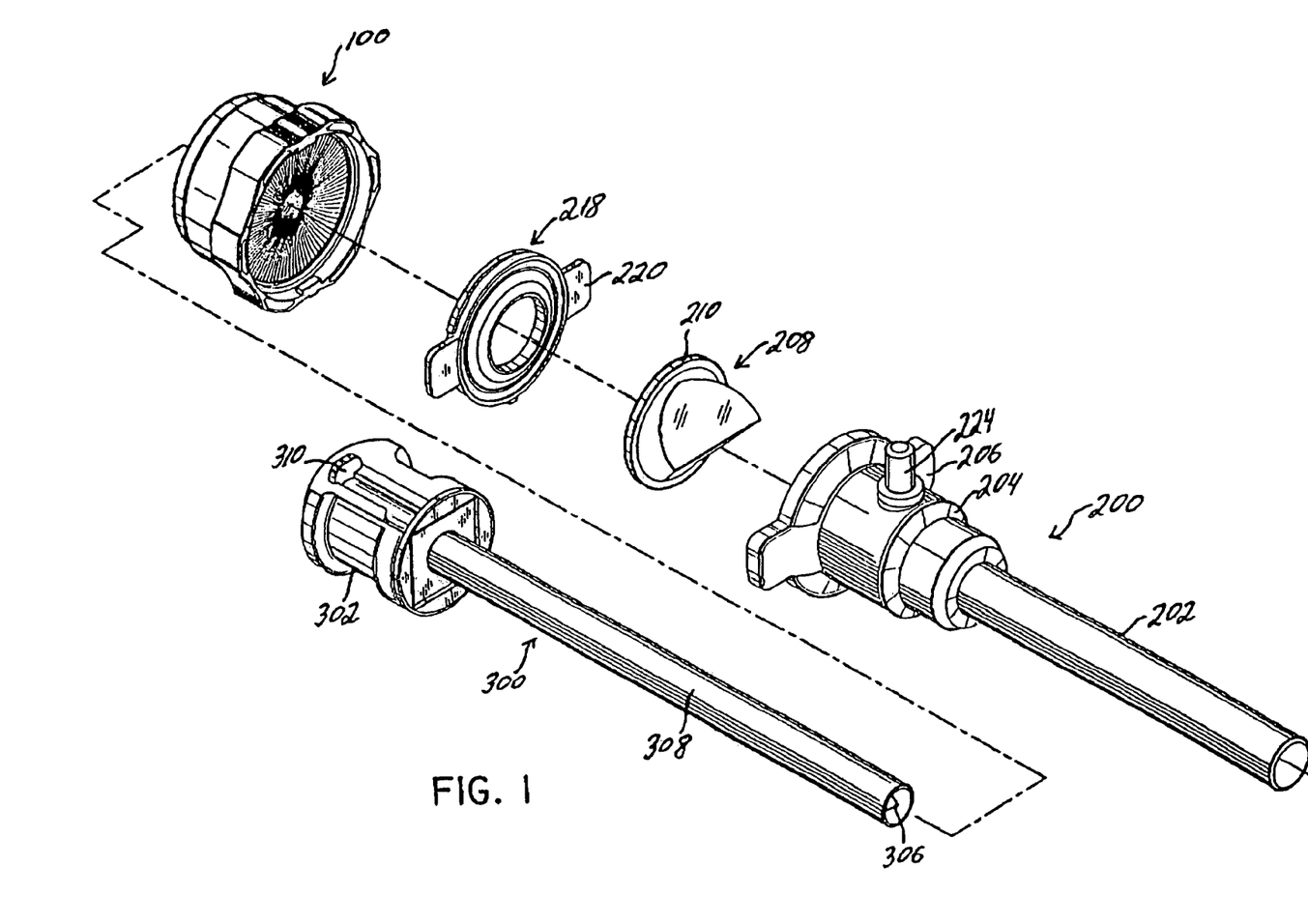
FIG. 1 is a perspective view with parts separated of a trocar assembly, cannula assembly and valve assembly constructed according to the principles of the present disclosure.

Referring initially to FIG. 1, there is illustrated a novel valve assembly 100 constructed in accordance with the principles of the present disclosure and intended to be used in combination with a conventional trocar assembly which generally includes a cannula assembly 200 and a trocar assembly 300.

The valve assembly 100 of the present disclosure, either alone or in combination with a valve unit/seal assembly internal to cannula assembly 200, and either integral with or detachably mounted to cannula assembly 200, provides a substantial seal between a body cavity of a patient and the outside atmosphere, both during and subsequent to insertion of an instrument through the cannula. Moreover, the valve assembly 100 of the present disclosure is capable of accommodating instruments of varying diameter, e.g. from 4.5 mm to 13 mm, by providing a substantial seal with each instrument when inserted. The valve assembly 100 is designed with a predetermined leak rate not to exceed 2 mm of mercury (Hg) in 20 seconds when the assembly 100 is manipulated by instruments of varying diameters, e.g., from about 4.5 mm to about 13 mm. The flexibility of the present valve assembly greatly facilitates endoscopic surgery where a variety of instruments having differing diameters are often needed during a single surgical procedure.

The valve assembly 100 is preferably detachably mountable to the proximal end of cannula assembly 200 disclosed herein. Thus, the surgeon can remove the valve assembly 100 from the cannula assembly 200 at any time during the surgical procedure and, similarly, mount the valve assembly 100 to the cannula when desired to provide a sealing engagement with an instrument to be inserted through the cannula. In addition, the valve assembly 100 may be readily adapted to be mounted to conventional cannulas of differing structures. The detachability of the valve assembly 100 from cannula assembly 200 facilitates specimen removal through cannula assembly 200 and reduces the profile of cannula assembly 200 when valve assembly 100 is not needed for the surgical procedure.

Figure 2:
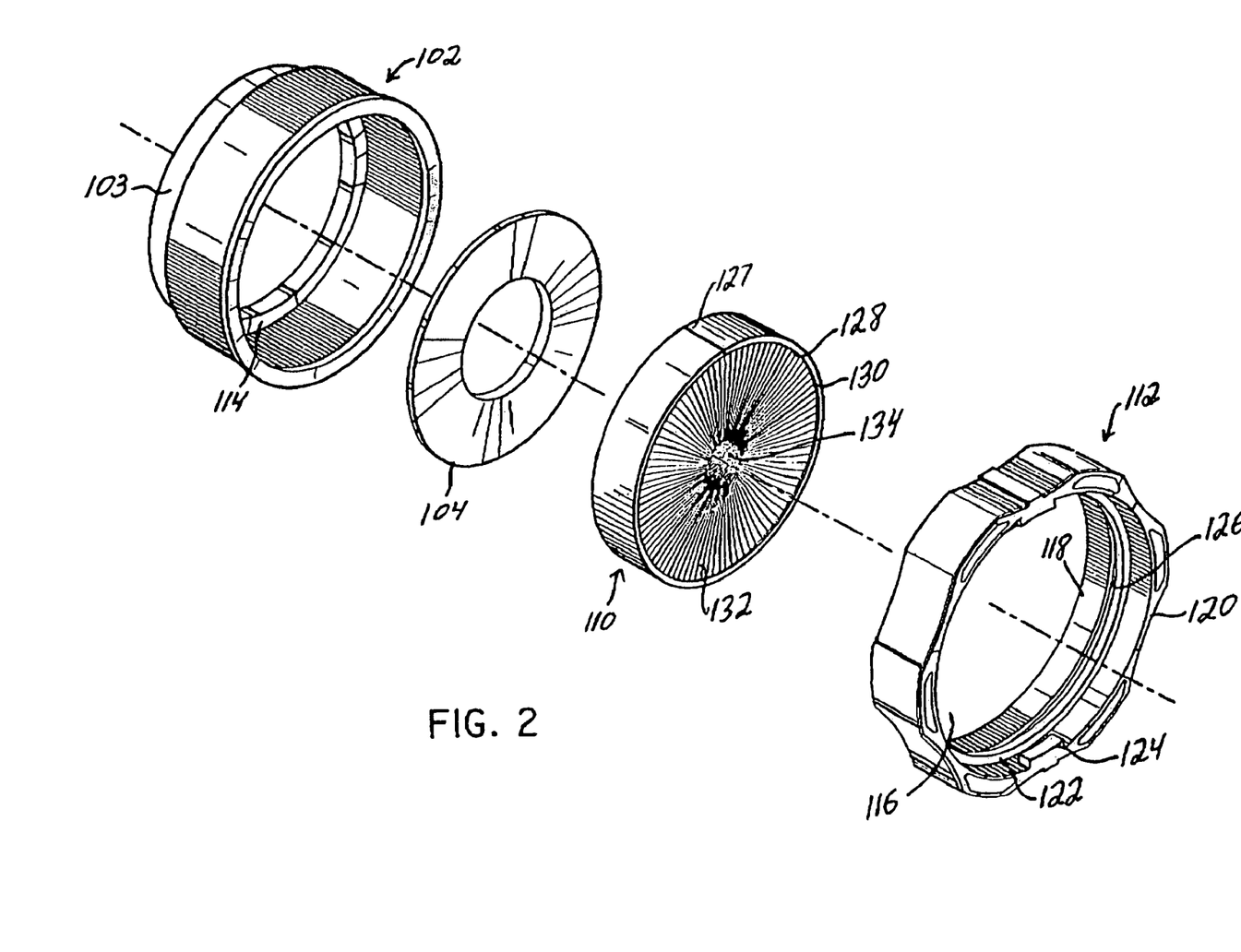
FIG. 2 is an enlarged perspective view with parts separated of the valve assembly of FIG. 1.

Referring now to FIG. 2, the novel valve assembly 100 of the present disclosure will be described in detail. Valve assembly 100 includes an end cap 102, a stabilizer plate 104, a seal member 110 and a seal housing 112. End cap 102, stabilizer plate 104 and seal housing 112 form the outer valve body of valve assembly 100, which houses the sealing and dilating component, i.e., seal member 110.

End cap 102 is generally cylindrically-shaped and includes a proximal end portion 103 defining a diameter which is less than the diameter of the remaining portion of the end cap and an inner peripheral ledge 114 which supports stabilizer plate 104. Seal housing 112 includes central opening 116, a proximal cylindrical portion 118 and a distal outer flange 120 having a scalloped surface to facilitate handling thereof. Cylindrical portion 118 is received within end cap 102 when the valve assembly 100 is fully assembled to enclose the sealing components. The distal end face of seal housing 112 includes a peripheral groove 122 and two opposed rib portions 124 extending radially inwardly adjacent the groove 122. Groove 122 and rib portions 124 assist in mounting valve assembly 100 to cannula assembly 200 as will be appreciated from the description provided below. The distal end face of seal housing 112 also includes a second groove 126 adjacent opening 116 for accommodating a portion of seal 110.

Figures 3, 4:
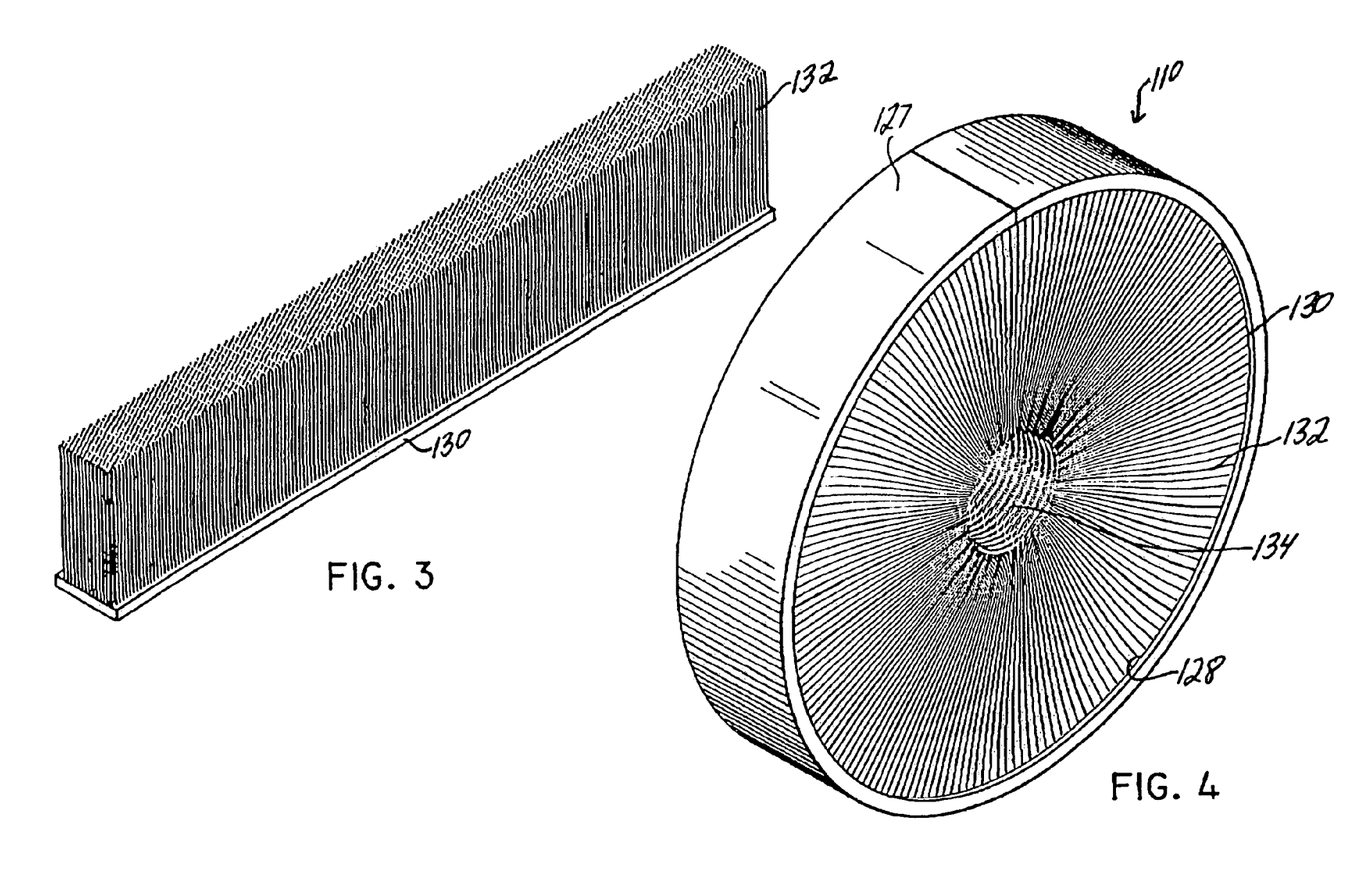
FIG. 3 is an enlarged perspective view of the resilient sealing structure of the valve assembly of FIG. 2.
FIG. 4 is an enlarged perspective view of the seal member shown in FIG. 2.

Referring now to FIGS. 2-4, sealing member 110 is cylindrical having an outer cylindrical surface 127 and an inner cylindrical surface 128. A substrate 130 having a plurality of bristle members 132 attached thereto, as shown by FIG. 3, lines the inner cylindrical surface 128 of the sealing member 110 defining aperture 134. Bristle members 132 are preferably fabricated. from an elastomeric material such as synthetic or natural rubber which is preferably sufficiently resilient to accommodate and provide a substantial seal with instruments of varying diameters inserted through aperture 134, e.g., instruments ranging in diameter from about 4.5 mm to about 13 mm, and sufficiently resilient to flex to accommodate manipulation of instrumentation inserted through aperture 134.

Referring now to FIG. 2 in conjunction with FIGS. 5 and 6, the assembling of the components of valve assembly 100 will be described in detail. Although in FIGS. 5 and 6 the valve assembly 100 is shown already mounted to cannula assembly 200, it is to be appreciated that generally valve assembly 100 is first assembled as a single unit and then mounted to the cannula assembly 200. The mounting of valve assembly 100 to cannula assembly 200 will be discussed below. Stabilizer plate 104 is positioned within end cap 102 such that the plate 104 rests on inner peripheral ledge 114 defined within the end cap 102. Thereafter, seal member 110 is positioned over stabilizer plate 104. Seal housing 112 is positioned over the entire unit with the cylindrical wall 118 of the seal housing 112 being received within the cylindrical wall of end cap 102. In this assembled condition, the distal end portion of the cylindrical wall of end cap 102 is received within an annular space defined between distal flange 120 of seal housing 112 and cylindrical wall 118 of seal housing 112 and retained therein by, e.g., friction or snap fit, thus retaining the valve assembly 100 in a fully assembled condition.

The valve assembly 100 now in its fully assembled condition can be mounted to cannula assembly 200. Referring to FIGS. 1, 5 and 6, cannula assembly 200 includes a cannula sleeve 202 and a cannula housing 204 mounted on one end of the sleeve 202. Cannula sleeve 202 defines a cannula passage in its interior and may be formed of stainless steel or other suitable rigid materials such as polycarbonate materials or the like.

Cannula housing 204 is rigidly secured to the proximal end of cannula sleeve 202 and defines a longitudinal opening for reception and passage of an elongated surgical instrument. The proximal end portion of the cannula housing 204 defines a generally circular cross-section and possesses diametrically opposed leg portions 206. A cannula seal 208 fabricated from a resilient material, e.g., rubber, is positioned within the interior of cannula housing 204. Seal 208 includes a circumferential flange portion 210 which rests on a correspondingly dimensioned circumferential ledge 212 within cannula housing 204. Seal 208 generally defines a duck bill shape having two planar tapering portions 214 which intersect at their distal ends to define abutment face 216. The planar tapering portions 214 may each include one or more inwardly directed, longitudinally oriented ribs to facilitate instrument passage. Abutment face 216 permits passage of the elongated object through the seal 208, but in the absence of an instrument, and particularly when cannula sleeve 202 is inserted into an insufflated body cavity, abutment face 216 forms a tight seal that isolates the insufflated cavity from the ambient surroundings. Seal 208 also includes at least one, preferably two, reinforcing ribs 215 to stabilize the seal. Ribs 215 are positioned to engage the instrument to guide the instrument through slits 216 and prevent piercing of the seal 208 by the tip of the instrument.

Cannula assembly 200 also includes a stabilizing plate 218 (FIG. 1) which is positioned against the flange portion 210 of seal 208 to provide support for seal 208 during introduction and withdrawal of an elongated instrument. Stabilizing plate 218 includes two diametrically opposed extensions 220 (FIG. 1) which are received within the correspondingly dimensioned leg portions 206 of the cannula housing 204. In the preferred embodiment, stabilizing plate 218 is securely attached to the cannula housing 204 at contact points along the extensions of the respective components by spot welding, adhesives or the like. Stabilizing plate 218 also includes a partial external annular rib or thread 222 (FIG. 6) adjacent its proximal end, the function of which will be appreciated from the description below.

A stop cock valve 224 may be incorporated as part of cannula housing 204 to permit the passage of insufflation gases through the cannula and into the body cavity. A suitable valve for this purpose is available from the Burron OEM Division of B. Braun Medical, Inc. (Model No. 55401022).

Figure 5:
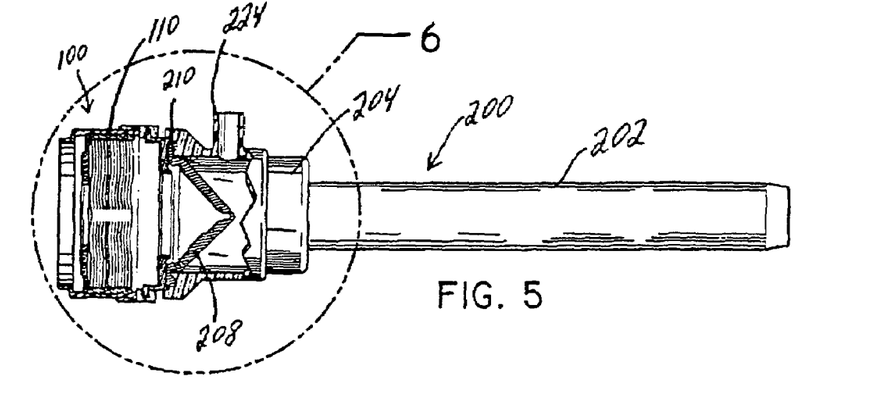
FIG. 5 is a side plan view in partial cross-section of the cannula housing and the valve assembly detachably mounted to the cannula housing.
Figure 6:
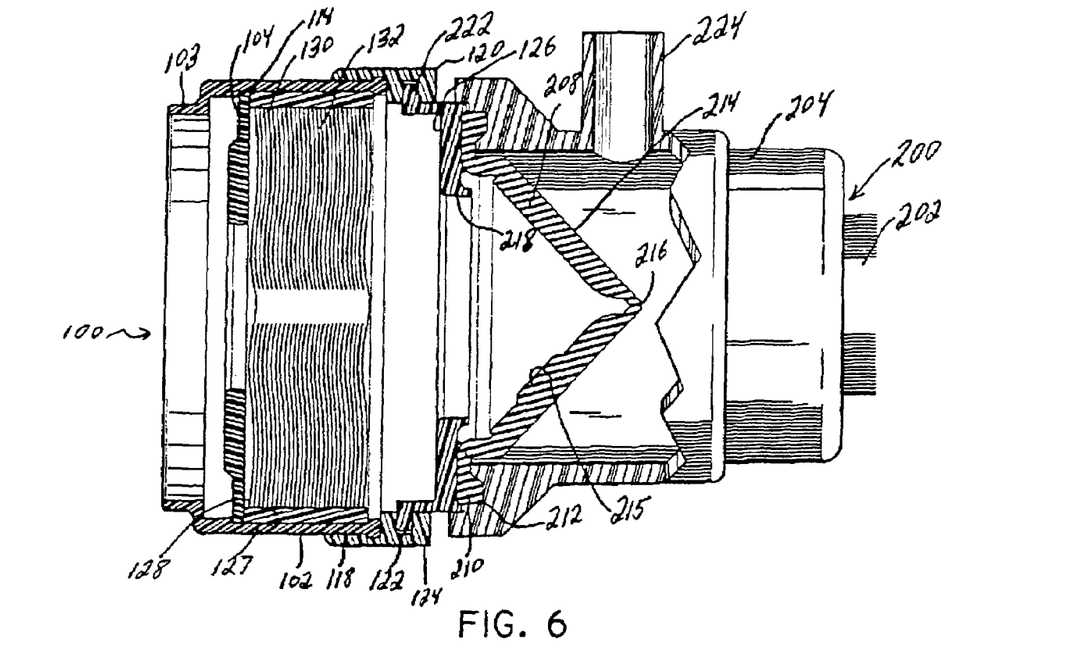
FIG. 6 is an enlarged, partial cross-sectional view of the area of detail as indicated in FIG. 5, illustrating the valve assembly and the cannula housing.

Referring still to FIGS. 1, 5 and 6, assembled valve assembly 100 is detachably mounted adjacent stabilizing plate 218 with the partial annular thread 222 of the stabilizing plate 218 being received within the peripheral groove 122 (FIG. 2) defined in the distal face of seal housing 112. The valve assembly 100 is rotated to cause engagement of the radially inwardly projecting rib portions 124 adjacent groove 122 with the partial annular thread 222 to releasably lock the valve assembly 200 to the cannula housing 204. Other means for detachably connecting the valve assembly 100 to cannula housing 204 can be readily determined by one skilled in the art such as screw threads, adhesives, bayonet locking, and the like.

Figure 6A:
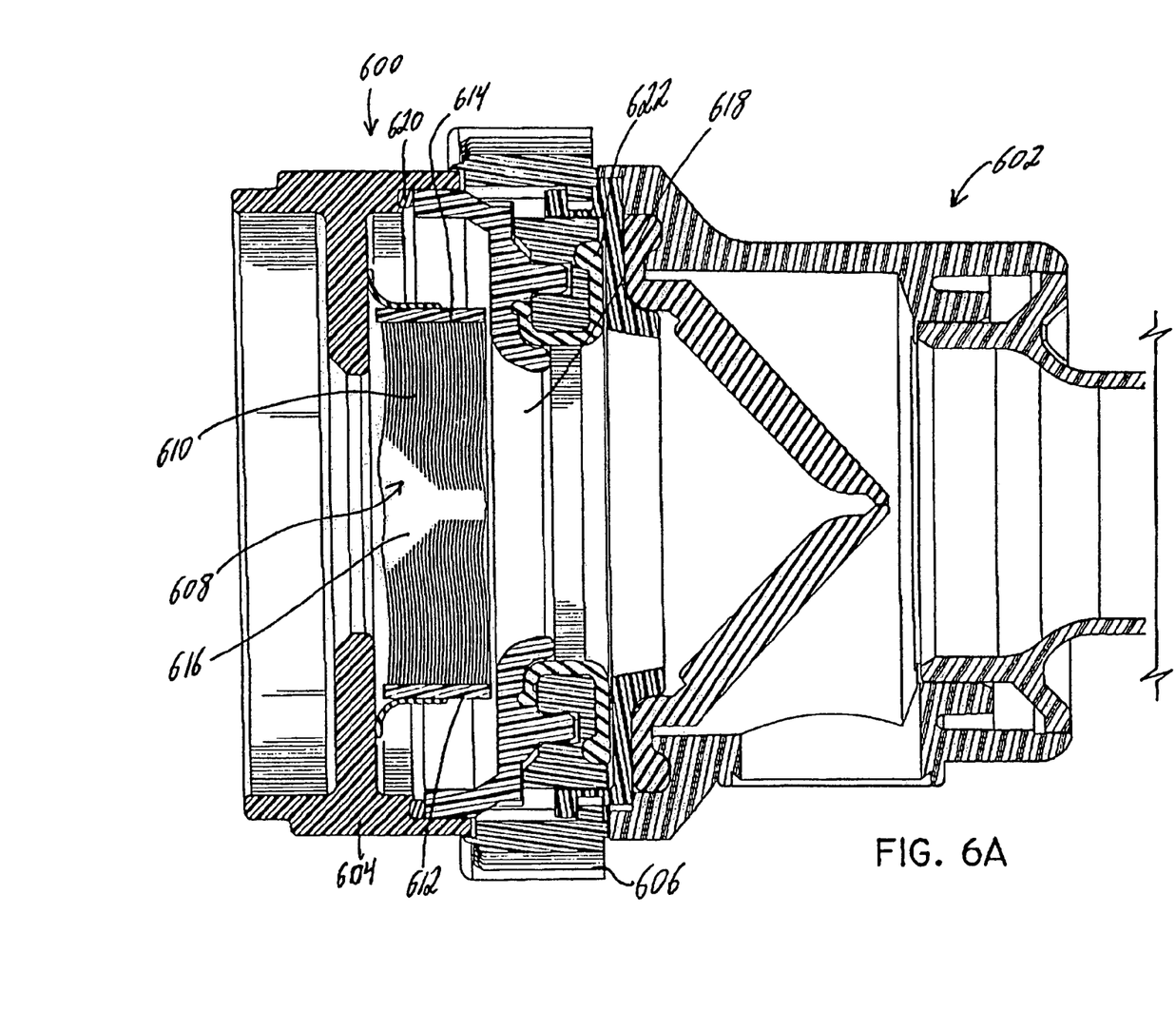
FIG. 6A is an enlarged, cross-sectional view of a first alternative valve assembly.
Figure 6B:
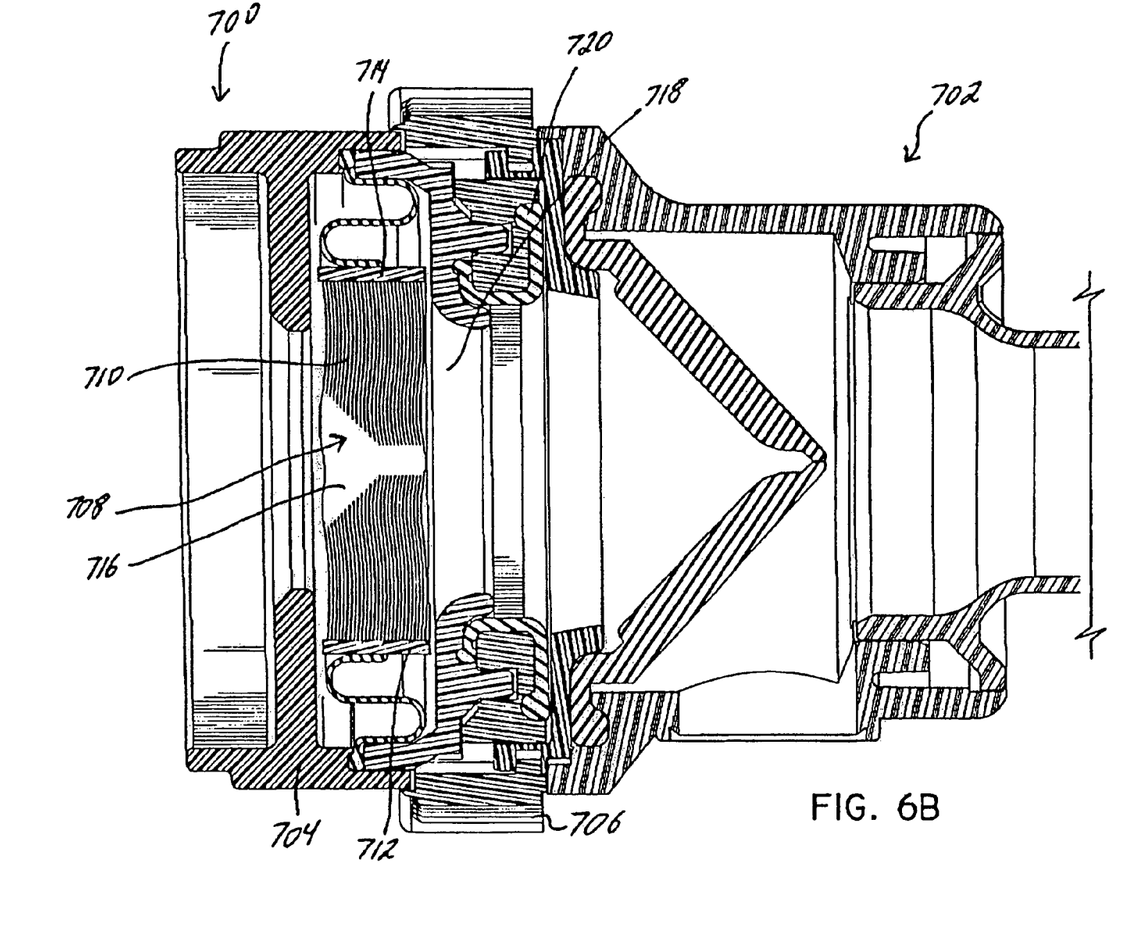
FIG. 6B is an enlarged, cross-sectional view of a second alternative valve assembly.

A first and second alternative embodiments for the valve assembly 100 are shown by FIGS. 6A and 6B, respectively. FIG. 6A shows a valve assembly designated generally by reference numeral 600. FIG. 6B shows a valve assembly designated generally by reference numeral 700. Valve assembly 600 is preferably detachably mountable to the proximal end of cannula assembly 602. Thus, the surgeon can remove the valve assembly 600 from the cannula assembly 602 at any time during the surgical procedure and, similarly, mount the valve assembly 600 to the cannula when desired. In addition, the valve assembly 600 may be readily adapted for mounting to conventional cannulas of differing structures. The detachability of the valve assembly 600 from the cannula assembly 602 facilitates specimen removal through the cannula assembly 602.

The valve assembly 600 includes a housing which is formed by the snap fitting together of end cap 604 and lower housing member 606. Preferably, the housing components of the valve assembly 600 are formed of a polycarbonate material such as ABS available from the General Electric Company. A seal member 608 is disposed within the valve assembly housing. The seal member 608 is constructed from bristle members 610 connected to substrates 612 and 614 on opposite sides. The seal member 608 includes a taper 616 to facilitate the insertion of a surgical instrument. The taper 616 can have an angle less than 90 degrees with respect to the central longitudinal axis of the valve assembly 600. Bristle members 610 sealingly engage to form a seal about the surgical instrument when inserted within valve assembly 600 and a seal within the valve housing and the external atmosphere.

A seal clamp 618 is provided within the housing components 604 and 606 which secures O-ring 620 and lower seal 622 with respect to the valve assembly 600. Lower seal 622 is provided at the distal end of lower housing member 606 and assists in the sealing engagement of valve assembly 600 to cannula assembly 602.

The valve assembly 700 is preferably detachably mountable to the proximal end of cannula assembly 702. Thus, the surgeon can remove the valve assembly 700 from the cannula assembly 702 at any time during the surgical procedure and, similarly, mount the valve assembly 700 to the cannula when desired in order to provide a sealing engagement with an instrument to be inserted through the cannula. In addition, valve assembly 700 may be readily adapted for mounting to conventional cannulas of differing structures. The detachability of the valve assembly 700 from the cannula assembly 702 facilitates specimen removal through cannula assembly 702. The valve assembly 700 includes a housing which is formed by the snap fitting together of end cap 704 and lower housing member 706. Preferably, the housing components of valve assembly 700 are formed of a polycarbonate material such as ABS available from the General Electric Company.

A seal member 708 is disposed within the valve assembly housing. Similarly to seal member 608, seal member 708 is constructed from bristle members 710 connected to substrates 712 and 714 on opposite sides. The seal member 708 includes a taper 716 facilitate the insertion of the surgical instrument. The taper 716 can have an angle less than 90 degrees with respect to the central longitudinal axis of the valve assembly 700. Bristle members 710 sealingly engage to form a seal about the surgical instrument when inserted within valve assembly 700 and a seal within the valve housing and the external atmosphere.

A seal clamp 718 is provided within the housing components 704 and 706. Seal clamp 718 is further described in commonly-assigned U.S. Provisional Application Ser. No. 60/045,412 filed on May 2, 1997 by Racenet et al., the contents of which are incorporated herein by reference. A lower seal 720 is provided at the distal end of lower housing member 706 and assists in the sealing engagement of valve assembly 700 to cannula assembly 702.

Figure 7:
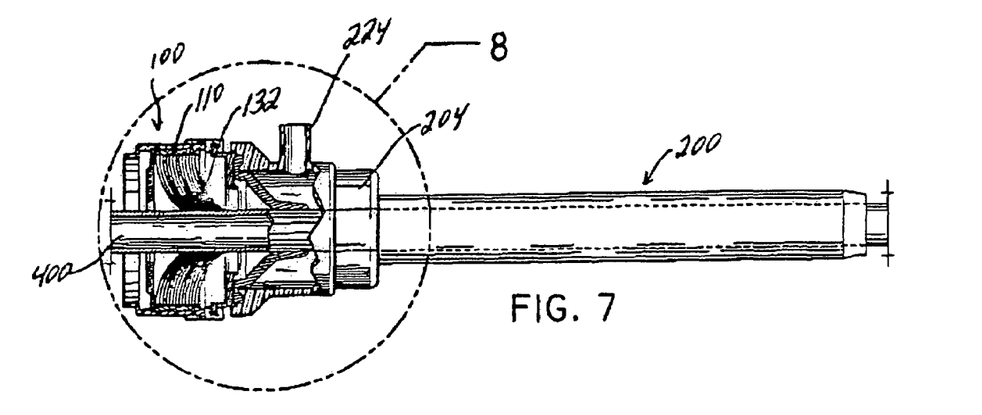
FIG. 7 is a view similar to FIG. 5 illustrating the introduction of an elongated object into the valve assembly and cannula assembly.
Figure 8:
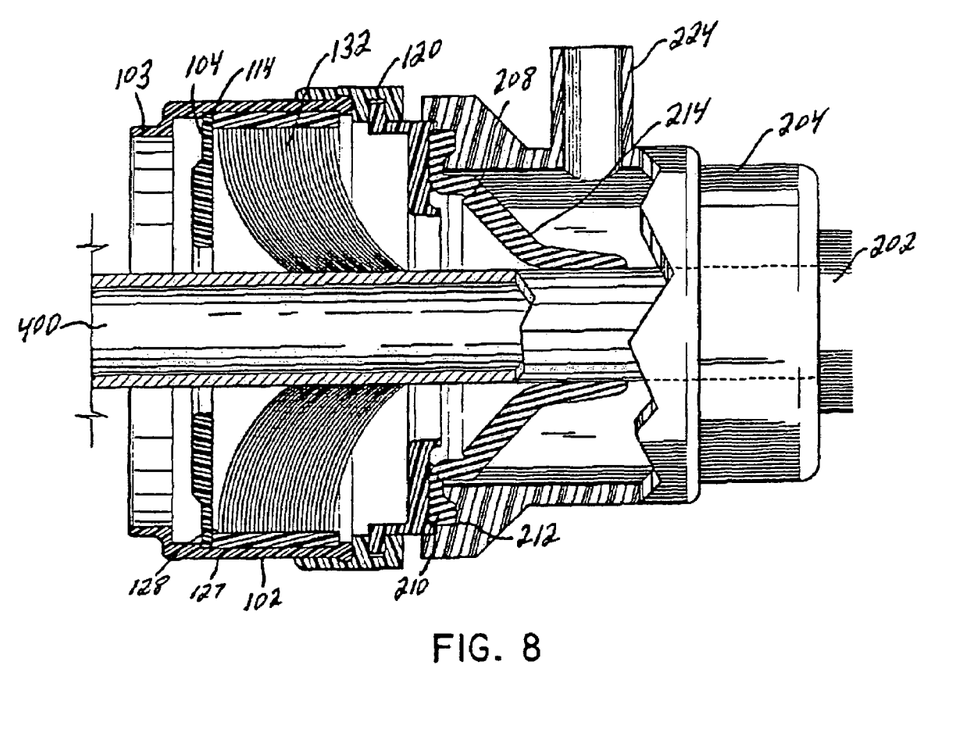
FIG. 8 is a view similar to FIG. 6 of the area of detail as indicated in FIG. 7, illustrating sealing engagement of a resilient sealing structure of the valve assembly with an elongated object.

Referring now to FIGS. 7 and 8, an elongated object such as a surgical instrument, identified generally by reference numeral 400, may be inserted through the valve assembly 100 and into the cannula assembly 200 to perform the desired surgical procedure. As the surgical instrument 400 enters the valve assembly 100, the tip of the surgical instrument 400 is engaged by the bristle members 132. Upon further advancement of the surgical instrument 400, the bristle members 132 are pivoted downwardly to increase the dimension of the aperture 134 to the degree necessary to accommodate instrument 400. The dimensions of the bristle members 132 and their flexibility permits relatively easy passage of instrument 400 through the valve assembly 100. The resilient seal member 110 sealingly engages to form a seal about the surgical instrument and a seal within the valve housing and the external atmosphere. Instrument 400 is advanced through cannula assembly 200 whereby the duckbill seal 208 of the cannula 200 also spreads to allow passage of instrument 400. Once positioned within the valve assembly 100 and cannula assembly 200, surgical instrument 400 may be maneuvered about the internal body cavity.

Figure 9:
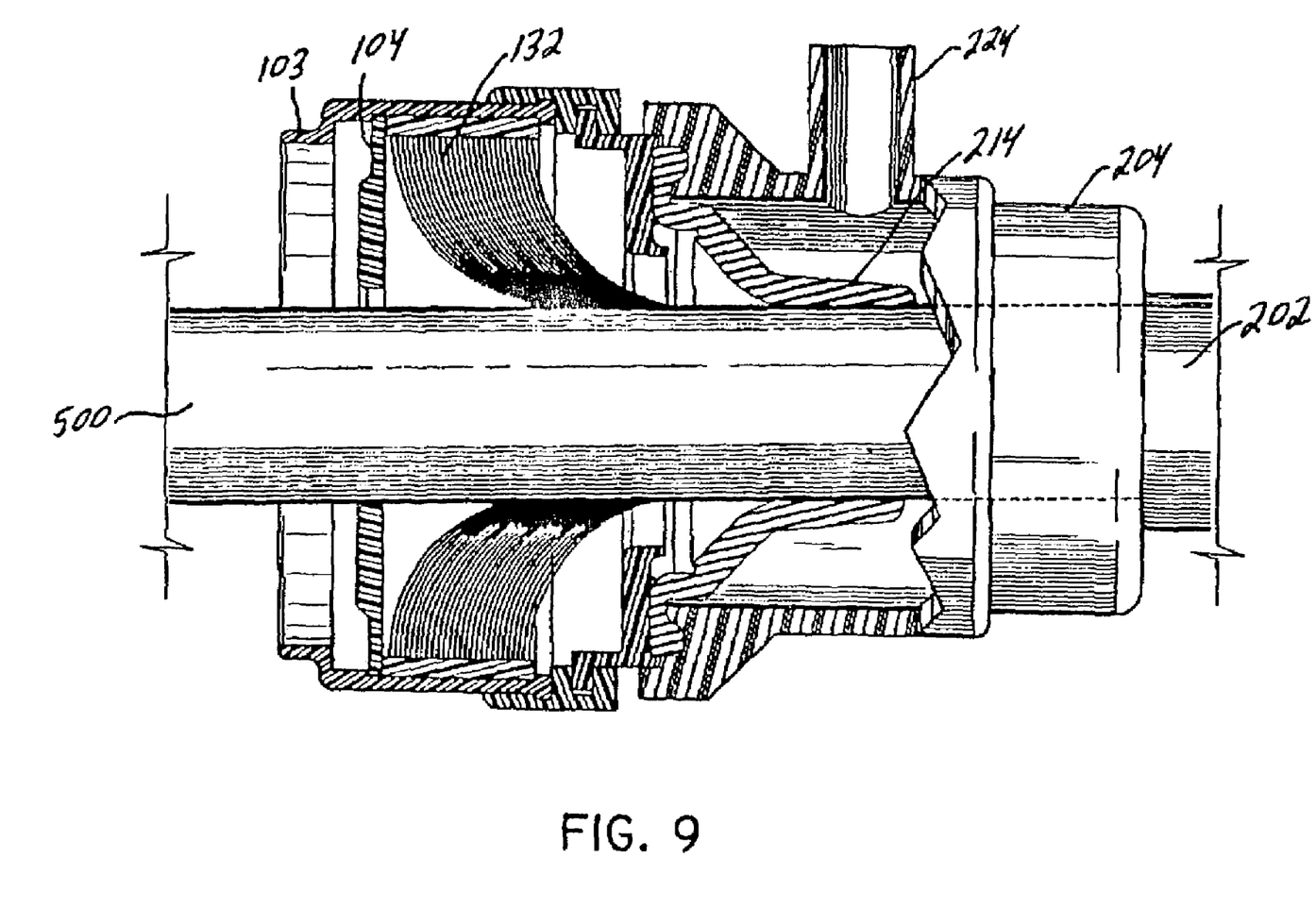
FIG. 9 is a view similar to FIG. 8, illustrating the adaptability of the valve assembly to radial movement of an elongated object in the cannula assembly.

As shown in FIG. 9, the valve assembly 100 permits limited unencumbered movement of instrument 400 in a radial direction (relative to the centerline of cannula sleeve 202) while still maintaining an adequate seal about the instrument. Thus, manipulation of the instrument 400 in any direction, either longitudinally or radially, to the extent permitted by the rigid housings and cannula sleeve 202, will not effect the integrity of the seal, since the resilient material of sealing member 110 will conform to the movements of the instrument and assume a shape necessary to retain a sealing contact with the instrument. FIG. 9 also shows that the seal member 110 can maintain an adequate seal about an instrument having a diameter that is greater than the diameter of the instrument shown in FIG. 8.

Figure 10:
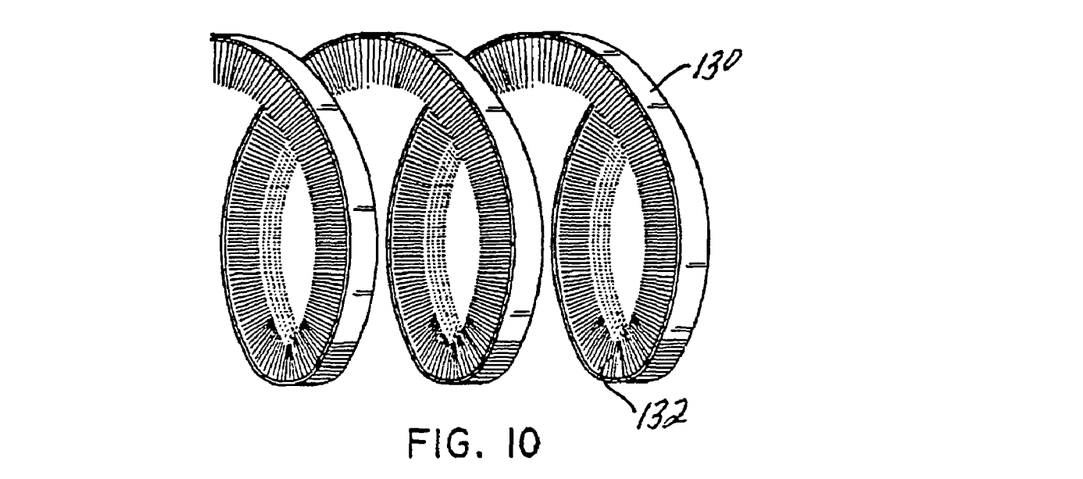
FIG. 10 is an enlarged perspective view of a resilient sealing structure having a spiral arrangement.
Figure 11:
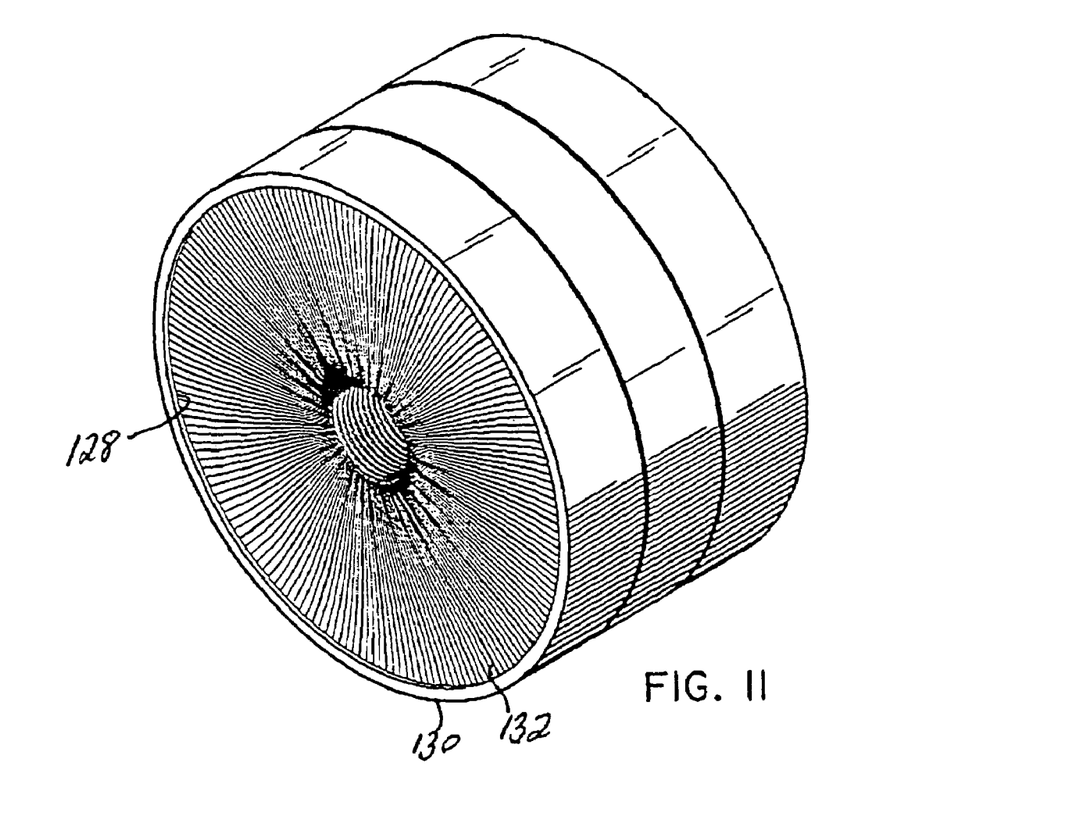
FIG. 11 is an enlarged perspective view of the resilient sealing structure of FIG. 10 in assembled form.
Figure 12:
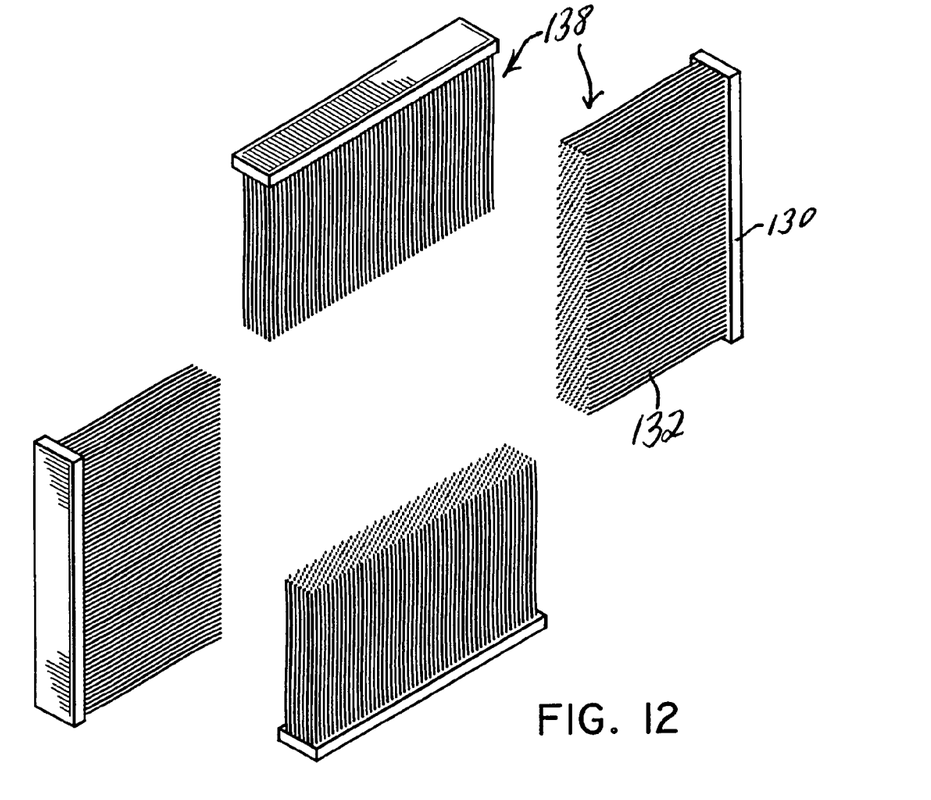
FIG. 12 is an enlarged perspective view of a further alternative embodiment of a resilient sealing structure having four individual parts.
Figure 13:
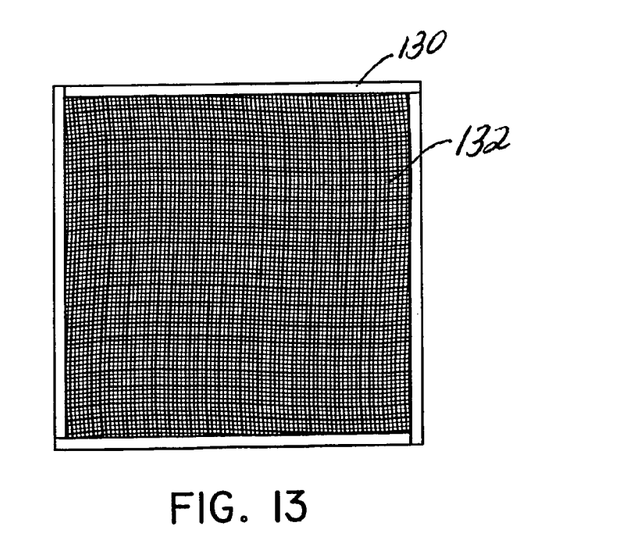
FIG. 13 is an enlarged perspective view of the resilient sealing structure of FIG. 12 where the four individual parts have been brought together to form a multi-array arrangement.

With reference to FIGS. 10-13, two alternative embodiments are shown for creating a seal using bristle members 132 connected to substrate 130. FIG. 10 shows the substrate 130 having a spiral arrangement and FIG. 11 shows the spiral arrangement of FIG. 10 in assembled form. FIG. 12 shows a resilient sealing structure having four individual parts 138 and FIG. 13 shows the resilient sealing structure shown in FIG. 12 arranged in a multi-array assembly.

While the above description contains many specifics, these specifics should not be construed as limitations on the scope of the presently disclosed valve system, but merely as an exemplification of preferred embodiments thereof. Those skilled in the art will envision other possible variations that are within the scope and spirit of the present disclosure as defined by the claims appended hereto.

What is claimed is:

1. An assembly for sealed reception of a surgical object into a body cavity of a patient, which comprises:
    a housing;
    a sleeve connected to the housing and dimensioned for introduction through body tissue to provide access to an underlying surgical site in a body cavity, the sleeve defining a longitudinal axis, the housing and the sleeve defining a longitudinal passage for reception and passage of the surgical object;
    a first seal member detachably mounted to the housing for forming a substantial sealing relation with the surgical object passing through longitudinal passage of the housing and the sleeve, the first seal member including a plurality of flexible bristle members mounted about the longitudinal axis to extend inwardly relative to the longitudinal axis, at least some of the bristle members configured to define an internal longitudinal taper whereby an internal dimension defined by the internal taper decreases along the longitudinal axis from proximal to distal, at least some of the remaining bristle members being arranged to define a longitudinal opening distal of the internal longitudinal taper and having an internal dimension which is substantially constant along the longitudinal axis, the internal longitudinal taper leading to the longitudinal opening; and
    a second seal member for sealing the longitudinal passage in the absence of the surgical object.

2. The assembly according to claim 1 wherein the at least some of the bristle members are coaxially mounted about the longitudinal axis to define the internal taper having a general frusto-conical configuration.

3. The assembly according to claim 2 wherein the at least some of the remaining bristle members are coaxially mounted about the longitudinal axis to define a substantially annular longitudinal opening, the internal taper leading to the substantially annular longitudinal opening.

4. The assembly according to claim 2 wherein the at least some of the remaining bristle members are coaxially mounted about the longitudinal axis to define a substantially circular longitudinal opening.

5. The assembly according to claim 1 wherein the first seal member includes a substrate, the bristle members extending from the substrate toward the longitudinal axis.

6. The assembly according to claim 5 wherein the first seal member is disposed within a seal housing, wherein the seal housing includes inner wall portions defining an internal recess, the first seal member being disposed in the internal recess.

7. The assembly according to claim 6 wherein the first seal member is adapted to laterally move within the internal recess.

8. The assembly according to claim 1 wherein the bristle members comprise an elastomeric material.

9. The assembly according to claim 1 wherein the longitudinal passage is configured to receive a surgical instrument.

10. The assembly according to claim 1 wherein the second seal member includes a cannula seal.

11. The assembly according to claim 1 wherein the longitudinal passage is configured to receive an instrument ranging between about 4 mm to about 12 mm in diameter.

12. The assembly according to claim 1 wherein the first seal member is configured to receive a surgical instrument.

13. The assembly according to claim 1 wherein the second seal member includes a duckbill seal.

* * * * *